(12) United States Patent
Rametsteiner et al.

(10) Patent No.: US 7,812,052 B2
(45) Date of Patent: Oct. 12, 2010

(54) STABLE AQUEOUS FORMULATION OF A PLATIN DERIVATIVE

(75) Inventors: Reinhard Rametsteiner, Unterach (AT); Heinz Schnait, Seewalchen (AT)

(73) Assignee: Ebewe Pharma Ges.m.b.H. NFG KG, Unterach (AT)

( * ) Notice: Subject to any disclaimer, the term of this patent is extended or adjusted under 35 U.S.C. 154(b) by 422 days.

(21) Appl. No.: 11/666,880

(22) PCT Filed: Oct. 28, 2005

(86) PCT No.: PCT/EP2005/011570

§ 371 (c)(1),
(2), (4) Date: May 8, 2007

(87) PCT Pub. No.: WO2006/048194

PCT Pub. Date: May 11, 2006

(65) Prior Publication Data

US 2007/0299132 A1    Dec. 27, 2007

(30) Foreign Application Priority Data

Nov. 2, 2004   (DE) .................. 10 2004 052 877

(51) Int. Cl.
*A61K 31/282* (2006.01)
*A61P 35/00* (2006.01)
*C07F 15/00* (2006.01)

(52) U.S. Cl. ...................... 514/492; 556/137
(58) Field of Classification Search ............... None
See application file for complete search history.

(56) References Cited

U.S. PATENT DOCUMENTS

| 4,169,846 | A | 10/1979 | Kidani et al. |
|---|---|---|---|
| 5,716,988 | A | 2/1998 | Ibrahim et al. |
| 6,306,902 | B1 | 10/2001 | Anderson et al. |
| 6,476,068 | B1 | 11/2002 | Lauria et al. |
| 2003/0109515 | A1 | 6/2003 | Lauria et al. |
| 2005/0074463 | A1 * | 4/2005 | Autran et al. ............ 424/185.1 |

FOREIGN PATENT DOCUMENTS

| EP | 0 774 963 | | 5/1997 |
|---|---|---|---|
| EP | 0 943 331 | | 6/2001 |
| WO | 01/15691 | | 3/2001 |
| WO | WO03/025166 | * | 3/2003 |
| WO | 03/047587 | | 6/2003 |

* cited by examiner

*Primary Examiner*—Brian-Yong S Kwon
*Assistant Examiner*—Bong-Sook Baek
(74) *Attorney, Agent, or Firm*—Wenderoth, Lind & Ponack, L.L.P.

(57) ABSTRACT

Disclosed is a stable aqueous formulation of a platin derivative, particularly oxaliplatin. The selected stabilizing additive is effective even in very small concentrations.

8 Claims, No Drawings

STABLE AQUEOUS FORMULATION OF A PLATIN DERIVATIVE

The invention relates to stable aqueous formulations of a platinum derivative, in particular of oxaliplatin, as well as their pharmaceutical application as pharmaceutical products.

Oxaliplatin is an antineoplastic agent disclosed in U.S. Pat. No. 4,169,846. Oxaliplatin is utilized alone or in combination with 5-FU and folinate especially for the treatment of metastasizing colorectal cancer and is preferably administered parenterally.

EP 774 963 A discloses pharmaceutically stable preparations of oxaliplatin for parenteral administration. The described solution of oxaliplatin in water has a pH value of 4.5 to 6 and is said to be free of any acidic or alkaline additive or buffer agent or other additive substance.

WO 03/047587 A discloses a formulation of oxaliplatin with an effective stabilizing quantity of lactic acid or its salts. In the examples, a concentration of 0.001 M to 0.0005 M of stabilization agent is utilized for the production of the formulation.

From EP 943 331 A formulations of oxaliplatin are known, which comprise a buffer additive of oxalic acid or an alkali metal salt of oxalic acid.

The stabilizing effect of oxalic acid or alkali metal salts of oxalic acid is contrasted with the use of other conventional buffer substances.

The conventional buffer substances utilized therein are citrate, sodium acetate, Tris, glycine and phosphate, each at a concentration of 0.1 M.

The invention addresses the problem of providing stable aqueous formulations of oxaliplatin which have improved stability compared to the known aqueous formulations.

The problem could unexpectedly be solved in that a stable aqueous formulation of oxaliplatin is obtained through the addition of conventional stabilizing additives at a very low concentration.

Subject matter of the invention is therefore a stable aqueous solution of oxaliplatin, characterized in that the aqueous solution comprises sodium acetate at a concentration of 0.005 to 0.00005 M as the stabilizing additive.

In the concentration range of 0.005 to 0.00005 M sodium acetate has an excellent stabilizing effect on the aqueous oxaliplatin solution. The aqueous oxaliplatin solution preferably comprises one of the stabilizing additives in a concentration of 0.0001 to 0.001 M.

The content of oxaliplatin in the aqueous stable formulation according to the invention may be 0.1-10 mg/mL, preferably 2-5 mg/mL.

The stable aqueous formulation preferably has a pH value of 4 to 6.

After a storage time of 3 months at 45° C. and 75% relative humidity, the stable aqueous formulations according to the invention have at least 95% of the original content of oxaliplatin.

The production of the preparation according to the invention takes place by dissolving oxaliplatin in water or in an aqueous solution of the corresponding stabilizing additive under agitation. If the substance is dissolved in water, addition of the stabilizing additive as an additional production step is necessary. The pH value is subsequently adjusted. In the last step the solution is sterilized by means of suitable sterilization methods and filled into appropriate containers (optionally under protective gas atmosphere). The utilized containers were previously cleaned and sterilized.

The stable aqueous formulations of oxaliplatin according to the invention are intended for the parenteral administration as "ready to use" formulations and, after dilution with established infusion media, such as for example 5% glucose, can be administered with the aid of conventional instruments.

EXAMPLES

Example 1

Solution with Phosphate 40 mg of oxaliplatin are mixed in a 20 mL volumetric flask with 1 mL phosphate solution (89.1 mg $Na_2HPO_4.2H_2O$ dissolved in 50 mL purified water; corresponds to 0.01 mol/L) and filled to 20 mL with purified water. The pH value is subsequently adjusted to 5.0 by means of 10% phosphoric acid. This solution is subsequently filtered through a 0.2 μm syringe filter, aliquoted in volumes of 2 mL into 5 mL vials, the vials are closed by crimping and stored under the conditions stated below.

Example 2

Solution with Citrate 40 mg of oxaliplatin are mixed in a 20 mL volumetric flask with 1 mL citrate solution (148.0 mg sodium citrate. $2H_2O$ dissolved in 50 mL purified water; corresponds to 0.01 mol/L) and filled to 20 mL with purified water. The pH value is subsequently adjusted to 5.0 by means of 10% citric acid. This solution is subsequently filtered through a 0.2 μm syringe filter, aliquoted in volumes of 2 mL into 5 mL vials, the vials are closed by crimping and stored under the conditions stated below.

Example 3

Solution with Acetate 80 mL of purified water are placed into a 100 mL volumetric flask. 0.0042 g of sodium acetate are subsequently added. 500 mg oxaliplatin are added to the solution and the solution is agitated until the oxaliplatin is completely dissolved. The pH value is subsequently adjusted to 5.0 with 1% acetic acid. After filling the volumetric flask with purified water up to the mark, the solution is filtered through a 0.2 μm syringe filter, aliquoted in volumes of 2 mL into 5 mL vials, the vials are closed by crimping and stored under the conditions stated below.

Example 4

Solution with Phosphate 40 mg of oxaliplatin are mixed in a 20 mL volumetric flask with 1 mL phosphate solution (89.1 mg $Na_2HPO_4.2H_2O$ dissolved in 50 mL purified water; corresponds to 0.01 mol/L) and filled to 20 mL with purified water. The pH value is subsequently adjusted to 4.0 by means of 10% phosphoric acid. This solution is subsequently filtered through a 0.2 μm syringe filter, aliquoted in volumes of 2 mL into 5 mL vials, the vials are closed by crimping and stored under the conditions stated below.

Example 5

Solution with Acetate 80 mL of purified water are placed into a 100 mL volumetric flask. 0.0042 g of sodium acetate are subsequently added. 500 mg oxaliplatin are added to the solution and the solution is agitated until oxaliplatin is completely dissolved. The pH value is subsequently adjusted to 6.0 with 1% acetic acid. After filling the volumetric flask with purified water up to the mark, the solution is filtered through a 0.2 μm syringe filter, aliquoted in volumes of 2 mL into 5 mL vials, the vials are closed by crimping and stored under the conditions stated below.

Oxaliplatin solutions with different stabilizing additives were produced analogously to the examples completed here and stored and tested under the conditions described in the following Tables.

Examination of content and purity was carried out by means of HPLC on a 5 μm octadecyl silica column. Evaluation was performed by means of UV detection at 210 nm with oxaliplatin as an external standard. A content of 100% corresponds to a concentration of 2 mg/mL of oxaliplatin.

The results are compiled in Tables 1-2.

TABLE 1

Content and purity after storage for 4 weeks at 40° C./75% relative humidity

|  | Content - Initial | Content 40° C./4 Weeks |
|---|---|---|
| 0.5 mM citric acid | 99.1% | 97.1% |
| 0.5 mM Na acetate | 101.7% | 99.9% |
| 0.5 mM tartaric acid | 99.7% | 97.2% |
| 0.5 mM phosphate | 97.6% | 96.8% |
| 0.5 mM succinic acid | 99.5% | 96.1% |
| 0.5 mM maleic acid | 101.8% | 98.7% |

TABLE 2

Content and purity after storage for 3 months at 40° C./75% relative humidity

|  | Content - Initial | Content 40° C./3 Months |
|---|---|---|
| 0.5 mM Na acetate | 101.7% | 99.5% |
| 0.5 mM tartaric acid | 99.7% | 97.5% |
| 0.5 mM succinic acid | 99.5% | 95.9% |
| 0.5 mM maleic acid | 101.8% | 97.3% |

Table 3 Content after 4 weeks of storage at 40° C./75% relative humidity
Additive=sodium acetate; pH=5.5

TABLE 3a

| Quantity Additive | Content - Initial | Content 4 Weeks |
|---|---|---|
| 0.05 mM Na acetate | 100.90% | 99.40% |
| 0.1 mM Na acetate | 99.60% | 97.90% |
| 0.5 mM Na acetate | 101.70% | 99.90% |
| 1 mM Na acetate | 101.20% | 99.10% |
| 5 mM Na acetate | 100.30% | 98.20% |
| without additive | 101.80% | 95.90% |

Content and purity after 3 months and 6 months at 25° C./60% relative humidity
Additive=sodium acetate; pH=5.5

TABLE 3b

| Quantity Additive | Content - Initial | Content 3 Months | Content 6 Months |
|---|---|---|---|
| 0.5 mM Na acetate | 100.10% | 99.60% | 99.50% |

As Tables 1-3 show, the sodium acetate utilized according to the invention already exhibits an excellent stabilizing effect at a low concentration of 0.0005 M.

The invention claimed is:

1. A stable aqueous solution of oxaliplatin, wherein the aqueous solution comprises as stabilizing additive sodium acetate at a concentration of 0.00005 to 0.005 M concentration.

2. The stable aqueous solution as claimed in claim 1, wherein the stabilizing additive is present at a concentration of 0.0001 to 0.001 M.

3. The stable aqueous solution of oxaliplatin as claimed in claim 1, wherein the content of oxaliplatin in the solution is 0.1-10 mg/mL.

4. The stable aqueous solution of oxaliplatin as claimed in claim 2, wherein the content of oxaliplatin in the solution is 0.1-10 mg/mL.

5. The stable aqueous solution of oxaliplatin as claimed in claim 1, wherein the content of oxaliplatin in the solution is 2-5 mg/mL.

6. The stable aqueous solution of oxaliplatin as claimed in claim 2, wherein the content of oxaliplatin in the solution is 2-5 mg/mL.

7. The stable aqueous solution of oxaliplatin as claimed in claim 1, wherein the solution has a pH value of 4 to 6.

8. A method for treating colorectal cancer which comprises parenterally administering the stable aqueous solution of oxaliplatin of claim 1 to a subject in need thereof.

* * * * *